United States Patent
Heer et al.

(10) Patent No.: US 8,278,324 B2
(45) Date of Patent: Oct. 2, 2012

(54) OXADIAZOLE DERIVATIVES ACTIVE ON SPHINGOSINE-1-PHOSPHATE (S1P)

(75) Inventors: Jag Paul Heer, Harlow (GB); Thomas Daniel Heightman, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 250 days.

(21) Appl. No.: 12/747,191

(22) PCT Filed: Dec. 19, 2008

(86) PCT No.: PCT/EP2008/067963
§ 371 (c)(1),
(2), (4) Date: Jun. 10, 2010

(87) PCT Pub. No.: WO2009/080724
PCT Pub. Date: Jul. 2, 2009

(65) Prior Publication Data
US 2010/0273827 A1   Oct. 28, 2010

(30) Foreign Application Priority Data
Dec. 21, 2007  (GB) .................................. 0725101.0

(51) Int. Cl.
C07D 413/04 (2006.01)
A61K 31/4725 (2006.01)
(52) U.S. Cl. ........................................ 514/307; 546/150
(58) Field of Classification Search .................. None
See application file for complete search history.

(56) References Cited

FOREIGN PATENT DOCUMENTS

| EP | 1760071 A | 3/2007 |
|---|---|---|
| EP | 1826197 A | 8/2007 |
| EP | 2003132 A | 12/2008 |
| WO | WO 2004/113330 | 12/2004 |
| WO | WO 2005/058848 | 6/2005 |
| WO | WO 2006/047195 | 5/2006 |
| WO | WO 2007/116866 | 10/2007 |
| WO | WO 2008/064337 | 5/2008 |
| WO | WO 2009/080725 | 7/2009 |
| WO | WO 2009/080728 | 7/2009 |
| WO | WO 2009/080729 | 7/2009 |
| WO | WO 2009/080730 | 7/2009 |

OTHER PUBLICATIONS

Nigel Cooke, et al: "Sphingosine 1-Phosphate Type 1 Receptor Modulators: Recent Advances and Therapeutic Potential" Annual Reports in Medicinal Chemistry, San Diego, US, vol. 42, Jan. 1, 2007, pp. 245-263, XP008102308; ISSN: 0065-7743.

Vachal Petr et al.: "Highly selective and potent agonists of sphingosine-1-phosphate 1 (S1P1) receptor." Bioorganic & Medicinal Chemistry Letters, Jul. 15, 2006, vol. 16, No. 14, pp. 3684-3687 ISSN: 0960-894X.

Yan Lin, et al.: "SAR studies of 3-arylpropionic acids as potent and selective agonists of sphingosine-1-phosphate receptor-1 (S1P1) with enhanced pharmacokinetic properties." Bioorganic & Medicinal Chemistry Letters Feb. 1, 2007, vol. 17 No. 3. pp. 828-831; ISSN: 0960-894X.

*Primary Examiner* — Zinna Northington Davis
(74) *Attorney, Agent, or Firm* — Linda E. Hall; John L. Lemanowicz

(57) ABSTRACT

The present invention relates to novel oxadiazole derivatives having pharmacological activity, processes for their preparation, pharmaceutical compositions containing them and their use in the treatment of various disorders.

3 Claims, No Drawings

OXADIAZOLE DERIVATIVES ACTIVE ON SPHINGOSINE-1-PHOSPHATE (S1P)

This application is a 371 of International Application No. PCT/EP2008/067963, filed 19 Dec. 2008, which claims the priority of GB Application No. GB 0725101.0 filed 21 Dec. 2007, which is incorporated herein in its entirety.

The present invention relates to novel oxadiazole derivatives having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P1 agonists on lymphocyte circulation through the lymph system. Treatment with S1P1 agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei et al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 Eur J Immunol 35:3570, Chiba 2005 Pharmacology and Therapeutics 108: 308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration and the use of S1P1 selective compounds (Hale et al 2004 Bioorganic & Medicinal Chemistry Letters 14:3501, Sanna et al 2004 JBC 279: 13839, Koyrakh et al 2005 American J Transplantation 5:529).

Hence, there is a need for S1P1 receptor agonist compounds with selectivity over S1P3 which might be expected to show a reduced tendency to induce bradycardia.

The following patent applications describe oxadiazole derivatives as S1P1 agonists: WO03/105771, WO05/058848, WO06/047195, WO06/100633, WO06/115188, WO06/131336, WO07/024922 and WO07/116866.

The following patent applications describe tetrahydroisoquinolinyl-oxadiazole derivatives as S1P receptor agonists: WO06/064757, WO06/001463, WO04/113330.

A structurally novel class of compounds has now been found which provides agonists of the S1P1 receptor.

The present invention therefore provides compounds of formula (I) or a pharmaceutically acceptable salt thereof thereof:

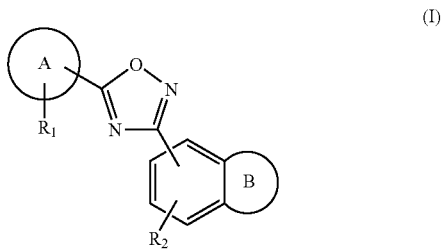

(I)

A is phenyl or a 5 or 6-membered heteroaryl ring;
$R_1$ is up to two substituents independently selected from halogen, $C_{(1-3)}$alkoxy, $C_{(1-3)}$fluoroalkyl, cyano, $C_{(1-3)}$fluoroalkoxy, $C_{(1-6)}$alkyl and $C_{(3-6)}$cycloalkyl;
$R_2$ is hydrogen, halogen or $C_{(1-4)}$alkyl;

B is selected from one of the following:

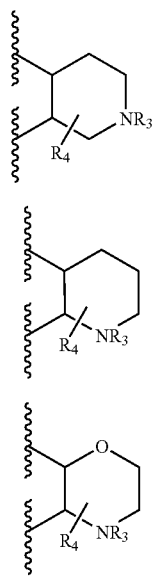

$R_3$ is hydrogen, $C_{(1-3)}$alkyl or $(CH_2)_{1-3}CO_2H$;
$R_4$ is hydrogen or $C_{(1-3)}$alkyl;
when $R_2$ or $R_4$ is alkyl it may be optionally interrupted by oxygen.

In one embodiment of the invention,
A is phenyl; and/or
$R_1$ is up to two substituents independently selected from chloro, isopropoxy, and cyano; and/or
$R_2$ is hydrogen; and/or
B is (a); and/or
$R_3$ is hydrogen, methyl or $(CH_2)_{1-3}CO_2H$; and/or
$R_4$ is hydrogen.
A is phenyl;
$R_1$ is up to two substituents independently selected from chloro, isopropoxy, and cyano;
$R_2$ is hydrogen or methyl;
B is (a);
$R_3$ is hydrogen, methyl or $(CH_2)_{1-3}CO_2H$;
$R_4$ is hydrogen.

In one embodiment A is phenyl. In another embodiment A is 3,4-disubstituted phenyl.

In one embodiment $R_1$ is two substituents one of which is $C_{(1-3)}$alkoxy, the other selected from halogen or cyano. In another embodiment $R_1$ is two substituents, one of which is isopropoxy and the other is selected from chloro or cyano. In another embodiment $R_1$ is two substituents selected from chloro, isopropoxy and cyano. In another embodiment $R_1$ is chloro and isopropoxy. In a further embodiment $R_1$ is chloro at the 3-position and isopropoxy at the 4-position when A is phenyl. In another embodiment $R_1$ is isopropoxy and cyano. In a further embodiment $R_1$ is cyano at the 3-position and isopropoxy at the 4-position when A is phenyl.

In one embodiment $R_2$ is hydrogen or methyl.
In one embodiment B is (a).
In one embodiment $R_3$ is hydrogen, methyl or $(CH_2)_{1-3}CO_2H$.
In one embodiment $R_4$ is hydrogen.

The term "alkyl" as a group or part of a group e.g. alkoxy or hydroxyalkyl refers to a straight or branched alkyl group in all isomeric forms. The term "$C_{(1-6)}$ alkyl" refers to an alkyl group, as defined above, containing at least 1, and at most 6 carbon atoms Examples of such alkyl groups include methyl, ethyl, propyl, iso-propyl, n-butyl, iso-butyl, sec-butyl, or tert-butyl. Examples of such alkoxy groups include methoxy, ethoxy, propoxy, iso-propoxy, butoxy, iso-butoxy, sec-butoxy and tert-butoxy.

Suitable $C_{(3-6)}$cycloalkyl groups include cyclopropyl, cyclobutyl, cyclopentyl and cyclohexyl.

As used herein, the term "halogen" refers to fluorine (F), chlorine (Cl), bromine (Br), or iodine (I) and the term "halo" refers to the halogen: fluoro (—F), chloro (—Cl), bromo(-Br) and iodo(-I).

The term "heteroaryl" represents an unsaturated ring which comprises one or more heteroatoms selected from O, N or S. Examples of 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

In certain of the compounds of formula (I), dependent upon the nature of the substituent there are chiral carbon atoms and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

It is understood that certain compounds of the invention contain both acidic and basic groups and may therefore exist as zwitterions at certain pH values.

Suitable compounds of the invention are:
5-(5-{3-chloro-4-[(1-methylethyl)oxy]phenyl}-1,2,4-oxadiazol-3-yl)-1,2,3,4-tetrahydroisoquinoline
2-[(1-methylethyl)oxy]-5-[3-(1,2,3,4-tetrahydro-5-isoquinolinyl)-1,2,4-oxadiazol-5-yl]benzonitrile
[5-(5-{3-cyano-4-[(1-methylethyl)oxy]phenyl}-1,2,4-oxadiazol-3-yl)-3,4-dihydro-2(1H)-isoquinolinyl]acetic acid
3-[5-(5-{3-cyano-4-[(1-methylethyl)oxy]phenyl}-1,2,4-oxadiazol-3-yl)-3,4-dihydro-2(1H)-isoquinolinyl]propanoic acid
4-[5-(5-{3-cyano-4-[(1-methylethyl)oxy]phenyl}-1,2,4-oxadiazol-3-yl)-3,4-dihydro-2(1H)-isoquinolinyl]butanoic acid
2-[(1-methylethyl)oxy]-5-[3-(2-methyl-1,2,3,4-tetrahydro-5-isoquinolinyl)-1,2,4-oxadiazol-5-yl]benzonitrile
[8-(5-{3-Chloro-4-[(1-methylethyl)oxy]phenyl}-1,2,4-oxadiazol-3-yl)-3,4-dihydro-2H -chromen-4-yl]acetic acid
3-[6-(5-{3-Chloro-4-[(1-methylethyl)oxy]phenyl}-1,2,4-oxadiazol-3-yl)-5-methyl-3,4-dihydro-2(1H)-isoquinolinyl]propanoic acid
[6-(5-{3-Chloro-4-[(1-methylethyl)oxy]phenyl}-1,2,4-oxadiazol-3-yl)-5-methyl-3,4-dihydro-2(1H)-isoquinolinyl] acetic acid
6-(5-{3-Chloro-4-[(1-methylethyl)oxy]phenyl}-1,2,4-oxadiazol-3-yl)-5-methyl-1,2,3,4-tetrahydroisoquinoline
2-[(1-Methylethyl)oxy]-5-[3-(5-methyl-1,2,3,4-tetrahydro-6-isoquinolinyl)-1,2,4-oxadiazol-5-yl]benzonitrile
[6-(5-{3-Cyano-4-[(1-methylethyl)oxy]phenyl}-1,2,4-oxadiazol-3-yl)-5-methyl-3,4-dihydro-2(1H)-isoquinolinyl] acetic acid 3-[6-(5-{3-cyano-4-[(1-methylethyl)oxy]phenyl}-1,2,4-oxadiazol-3-yl)-5-methyl-3,4-dihydro-2(1H)-isoquinolinyl]propanoic acid or pharmaceutically acceptable salts thereof.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolite or residue thereof.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

Pharmaceutically acceptable addition salts may be prepared conventionally by reaction with the appropriate acid or acid derivative. Pharmaceutically acceptable salts with bases may be prepared conventionally by reaction with the appropriate inorganic or organic base.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Included within the scope of the invention are all salts, solvates, hydrates, complexes, polymorphs, prodrugs, radio-labelled derivatives, stereoisomers and optical isomers of the compounds of formula (I).

The potencies and efficacies of the compounds of this invention for the S1P1 receptor can be determined by GTPγS assay performed on the human cloned receptor as described herein. Compounds of formula (I) have demonstrated agonist activity at the S1P1 receptor, using functional assays described herein.

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes (herein after referred to as the "Disorders of the Invention").

Compounds of formula (I) and their pharmaceutically acceptable salts are therefore of use in the treatment of lupus erythematosis.

Compounds of formula (I) and their pharmaceutically acceptable salts are therefore of use in the treatment of psoriasis.

Compounds of formula (I) and their pharmaceutically acceptable salts are therefore of use in the treatment of multiple sclerosis.

It is to be understood that "treatment" as used herein includes prophylaxis as well as alleviation of established symptoms.

Thus the invention also provides compounds of formula (I) or pharmaceutically acceptable salts thereof, for use as therapeutic substances, in particular in the treatment of the conditions or disorders mediated via the S1P1 receptor. In particular the invention provides a compound of formula (I) or a pharmaceutically acceptable salt thereof for use as a therapeutic substance in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes.

Compounds of formula (I) and their pharmaceutically acceptable salts are of use as therapeutic substances in the treatment of lupus erythematosis.

Compounds of formula (I) and their pharmaceutically acceptable salts are of use as therapeutic substances in the treatment of psoriasis.

Compounds of formula (I) and their pharmaceutically acceptable salts are of use as therapeutic substances in the treatment of multiple sclerosis.

The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof. In particular the invention provides a method of treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes, which comprises administering to the sufferer a therapeutically safe and effective amount of a compound of formula (I) or a pharmaceutically acceptable salt thereof.

The invention provides a method of treatment of lupus erythematosis, which comprises administering to the sufferer a therapeutically safe and effective amount of a compound of formula (I) or a pharmaceutically acceptable salt thereof.

The invention provides a method of treatment of psoriasis, which comprises administering to the sufferer a therapeutically safe and effective amount of a compound of formula (I) or a pharmaceutically acceptable salt thereof.

The invention provides a method of treatment of multiple sclerosis, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the S1P1 receptor.

In particular the invention provides a compound of formula (I) or a pharmaceutically acceptable salt thereof for use in the manufacture of a medicament for use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes.

Compounds of formula (I) and their pharmaceutically acceptable salts are of use in the manufacture of a medicament for use in the treatment of lupus erythematosis.

Compounds of formula (I) and their pharmaceutically acceptable salts are of use in the manufacture of a medicament for use in the treatment of psoriasis.

Compounds of formula (I) and their pharmaceutically acceptable salts are of use in the manufacture of a medicament for use in the treatment of multiple sclerosis.

In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salts thereof and a sterile vehicle. Formulations for injection may be presented in unit dosage form e.g. in ampoules or in multi-dose, utilising a compound of the invention or pharmaceutically acceptable derivatives thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts thereof may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof, may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

Compounds of formula (I) or pharmaceutically acceptable salts thereof may be used in combination preparations. For example, the compounds of the invention may be used in combination with cyclosporin A, methotrexate, steriods, rapamycin, proinflammatory cytokine inhibitors, immunomodulators including biologicals or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labeled reagent.

In a further aspect, this invention provides processes for the preparation of a compound of formula (I).

Compounds of formula (I) wherein B is

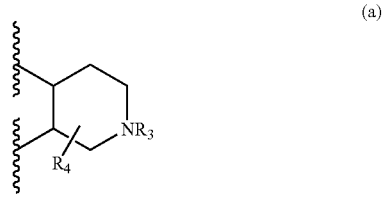

(a)

and $R_3$ is $(CH_2)_{1-3}CO_2H$ may be prepared according to Scheme 1, wherein $R_1$, $R_2$, $R_4$ and A are as defined for formula (I), n is 3, hal is chloro, bromo or iodo, P is a protecting group and R represents an alkyl group (eg ethyl or tert-butyl).

Scheme 1

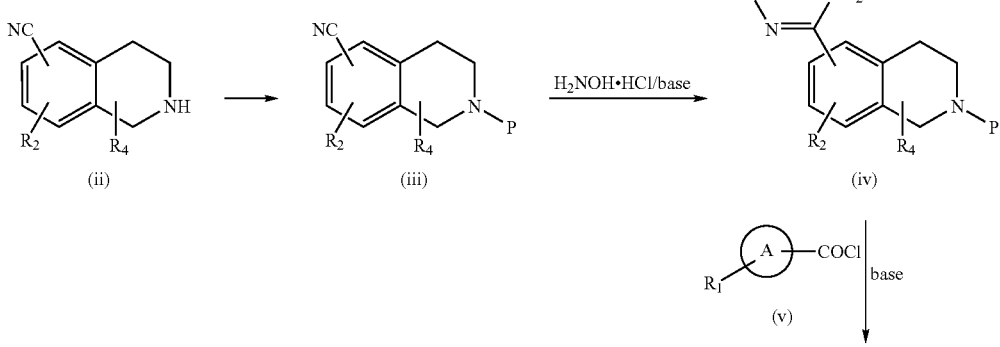

-continued

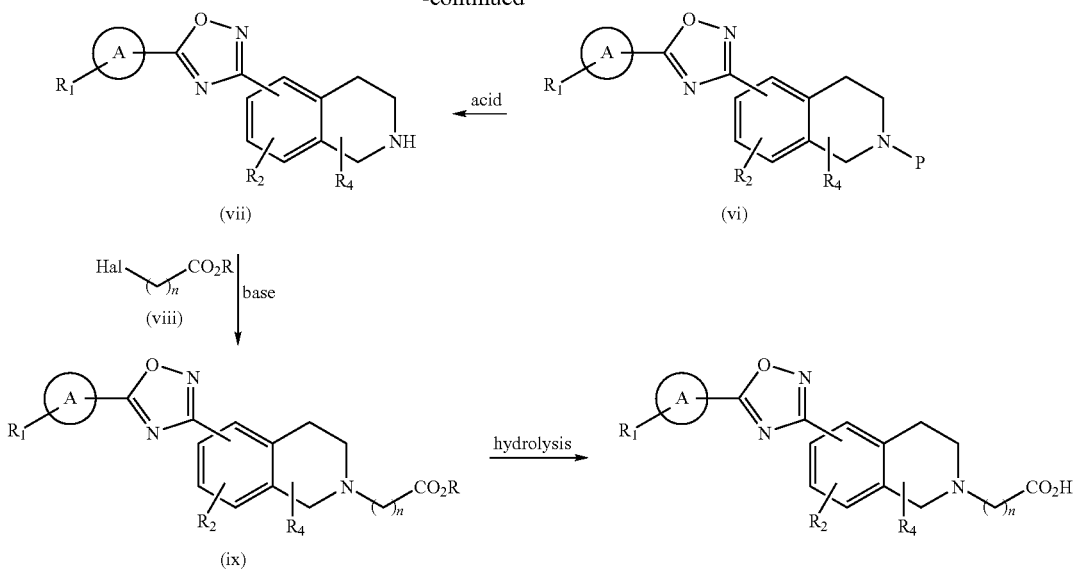

Compounds of formula (ii) (for example prepared as described in Tetrahedron (2006), 62(29), 6869-6875) may be converted to a suitable protected derivative (iii), where P is for example t-butoxycarbonyl, using a suitable protecting reagent such as bis(1,1-dimethylethyl)dicarbonate. Compounds of formula (iii) may be converted to compounds of formula (iv) by reaction with hydroxylamine in the presence of a suitable base such as sodium bicarbonate. Compounds of formula (iv) may be converted to compounds of formula (vi) by reaction with an acid chloride of formula (v) in the presence of a suitable base such as N,N-diisopropylethylamine, optionally in the presence of a catalyst such as 4-dimethylaminopyridine. The reaction may be carried out at room temperature initially followed by heating to effect cyclisation to the oxadiazole. Compounds of formula (vi) may be deprotected to give compounds of formula (vii), for example with a suitable acid such as hydrochloric acid where P represents t-butoxycarbonyl. Compounds of formula (vii) may be converted into compounds of formula (ix) by reaction with an alkylating agent of formula (viii) in the presence of a suitable base such as caesium carbonate. Compounds of formula (ix) may be converted into certain compounds of formula (I) by hydrolysis with a suitable base such as lithium hydroxide or (for R=t-butyl) a suitable acid such as hydrochloric acid or trifluoroacetic acid. Compounds of formula (v) are either known compounds or may be prepared by conventional means from the corresponding acids, which are themselves either known compounds or may be prepared by conventional means.

Compounds of formula (iii) wherein $R_2$ is in the 5-position and the cyano group is in the 6-position of the tetrahydroisoquinoline ring system may be prepared as shown in Scheme 2, wherein $R_1$ is defined for formula (I), $R_4$ is hydrogen and P is a protecting group.

Scheme 2

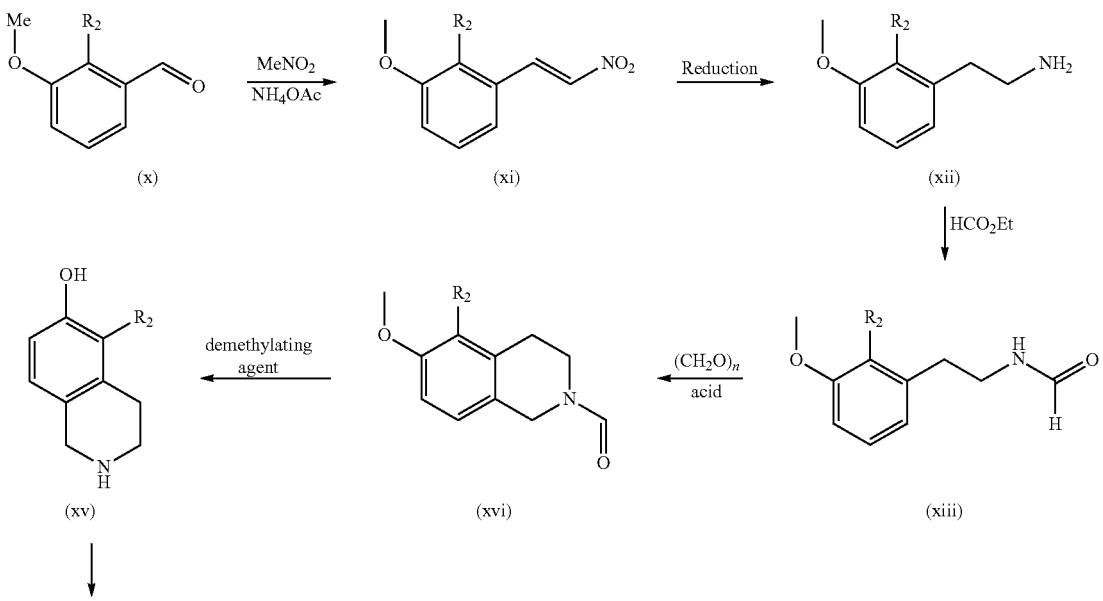

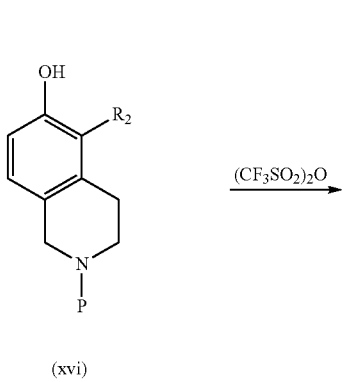

Compounds of formula (x) may be converted to compounds of formula (xii) by reaction with nitromethane in the presence of a suitable base such as ammonium acetate. Compounds of formula (xi) may be converted to compounds of formula (xii) by reduction with a suitable reducing agent such as lithium borohydride in the presence of chlorotrimethylsilane. Compounds of formula (xii) may be converted to compounds of formula (xiii) by reaction with a suitable formylating agent such as ethyl formate. Compounds of formula (xiii) may be converted to compounds of formula (xiv) by reaction with a suitable formaldehyde source such as paraformaldehyde, in the presence of a suitable acid catalyst such as formic acid.

Compounds of formula (xiv) may be converted to compounds of formula (xv) by reaction with a suitable demethylating agent such as boron tribromide.

Compounds of formula (xv) may be converted to suitable protected derivatives of formula (xvi) where P is for example t-butoxycarbonyl, using a suitable protecting reagent such as bis(1,1-dimethylethyl)dicarbonate. Compounds of formula (xvi) may be converted to compounds of formula (xvii) by reaction with a suitable trifluoromethanesulphonylating agent such as trifluoromethanesulphonic anhydride.

Compounds of formula (xvii) may be converted to compounds of formula (iii) (wherein $R_2$ is in the 5-position, $R_4$ is hydrogen and the cyano group is in the 6-position) by reaction with a suitable cyanide source such as zinc cyanide in the presence of a suitable catalyst such as tetrakis(triphenylphosphine)palladium (0).

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Abbreviations:
g—grams
mg—milligrams
ml—millilitres
ul—microlitres
MeCN—acetonitrile
MeOH—methanol
EtOH—ethanol
Et$_2$O—diethyl ether
EtOAc—ethyl acetate
DCM—dichloromethane
DIAD—diisopropyl azodicarboxylate
DIPEA—N,N-diisopropylethylamine
DMAP—N,N-dimethyl-4-pyridinamine
DME—1,2-bis(methyloxy)ethane
DMF—N,N-dimethylformamide
DMSO—dimethylsulphoxide
EDAC—N-(3-Dimethylaminopropyl)-N'-ethylcarbodiimide hydrochloride
EDC—N-(3-Dimethylaminopropyl)-N'-ethylcarbodiimide hydrochloride
EDCI—N-(3-Dimethylaminopropyl)-N'-ethylcarbodiimide hydrochloride
HOBT/HOBt—Hydroxybenzotriazole
IPA—isopropylalcohol
NCS—N-chlorosuccinimide
PyBOP—Benzotriazol-1-yl-oxytripyrrolidinophosphonium hexafluorophosphate
THF—tetrahydrofuran
dba—dibenzylidene acetone
RT—room temperature
° C.—degrees Celsius
M—Molar
H—proton
s—singlet
d—doublet
t—triplet
q—quartet
MHz—megahertz
MeOD—deuterated methanol
LCMS—Liquid Chromatography Mass Spectrometry
LC/MS—Liquid Chromatography Mass Spectrometry
MS—mass spectrometry
ES—Electrospray
MH$^+$—mass ion+H$^+$
MDAP—mass directed automated preparative liquid chromatography.
sat.—saturated
Boc—tert-butyloxycarbonyl
SCX or SCX-3—solid phase extraction (SPE) column with benzene sulfonic acid residues immobilised on the solid phase (eg. IST Isolute™ columns).

General Chemistry Section

The methods described below are given for illustrative purposes, intermediates in the preparation of the examples may not necessarily have been prepared from the specific batches described.

PREPARATION 1

1,1-dimethylethyl 5-[(hydroxyamino)(imino)methyl]-3,4-dihydro-2(1H)-isoquinolinecarboxylate

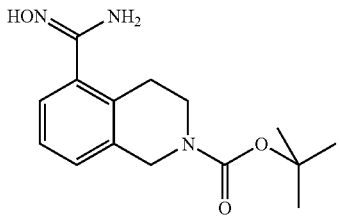

1,2,3,4-tetrahydro-5-isoquinolinecarbonitrile hydrochloride (5.0 g/25.7 mmol, available from Fluorchem) was partitioned between DCM (100 mL) and 2N NaOH. The DCM layer was collected, dried (hydrophobic frit) and evaporated. The free base, 1,2,3,4-tetrahydro-5-isoquinolinecarbonitrile was dissolved in dry DCM (100 mL) and treated with bis(1,1-dimethylethyl)dicarbonate (1.1 equiv, 6.17 g). The reaction was stirred at RT under argon for 18 h, washed with with 2N NaOH (100 mL), 2N HCl (100 mL), dried (hydrophobic frit) and evaporated to give the crude 1,1-dimethylethyl-5-cyano-3,4-dihydro-2(1H)-isoquinolinecarboxylate which was used without further purification (LCMS 100%, NMR 2:1 mixture with tBuOH). Isolated yield 7.58 g. $^1$H NMR (400 MHz, CDCl$_3$) δ (inter alia) 7.52 (1H, d), 7.35-7.16 (2H, m), 4.60 (2H, br.s), 3.71 (2H, t), 3.04 (2H, t), 1.5 (9H, s); m/z (API-ES) 203 [M+H-56]$^+$.

The crude material from above, hydroxylamine.HCl (14.31 g, 206 mmol) and sodium bicarbonate (21.63 g, 257 mmol) were added to a 500 mL round bottomed flask containing ethanol (200 mL). The reaction mixture was heated at 65° C. for 24 hours. The cooled reaction was evaporated and partitioned between DCM (2×100 mL) and water (100 mL). The combined DCM layers were collected and dried. Analysis by LC/MS showed the material to be ~80% pure. The material was dissolved in ethanol (100 mL) and filtered to remove undissolved impurities. Analysis by LC/MS showed the material to be ~92% pure. 1,1-dimethylethyl 5-[(hydroxyamino)(imino)methyl]-3,4-dihydro-2(1H)-isoquinolinecarboxylate was used without further purification. $^1$H NMR (400 MHz, CDCl$_3$) δ 7.82 (1H, br.s), 7.36-7.16 (3H, m), 4.80 (2H, br.s), 4.58 (2H, br.s), 3.59 (2H, br.t), 2.98 (2H, t), 1.49 (9H, s); m/z (API-ES) 292 [M+H]$^+$.

PREPARATION 2

Methyl 3-chloro-4-[(1-methylethyl)oxy]benzoate

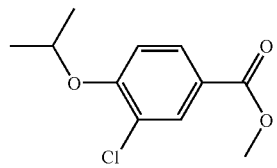

Methyl 3-chloro-4-hydroxybenzoate (50 g, 0.27 mole), K$_2$CO$_3$ (74 g, 0.54 mole) and iodopropane (29.5 ml, 0.23 mole) were stirred at room temperature in DMF (100 mL). After 18 hours, the solvent was removed by evaporation under vacuum and the residue was chromatographed over a column of silica 60 in EtOAc/hexane (1:1) to give the title compound as an oil (55 g, 90%). $^1$H NMR (400 MHz, CDCl$_3$) δ 8.05 (1H, d), 7.89 (1H, dd), 6.94 (1H, d), 4.60-4.72 (1H, m), 3.89 (3H, s), 1.41 (6H, d); m/z (API-ES) 229 [M+H]$^+$.

PREPARATION 3

1,1-dimethylethyl 5-(5-{3-chloro-4-[(1-methylethyl)oxy]phenyl}-1,2,4-oxadiazol-3-yl)-3,4-dihydro-2(1H)-isoquinolinecarboxylate

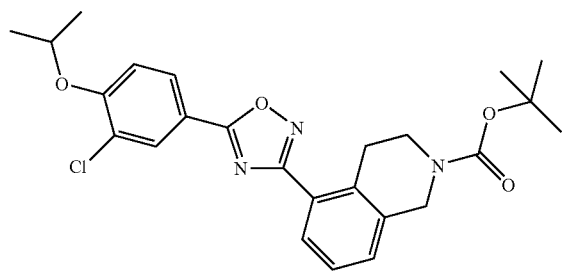

1,1-dimethylethyl 5-[(hydroxyamino)(imino)methyl]-3,4-dihydro-2(1H)-isoquinoline carboxylate (Preparation 1)(2 g, 6.86 mmol) was dissolved in tetrahydrofuran (THF) (100 mL) and stirred with sodium hydride (60% dispersion, 0.302 g, 7.55 mmol) under argon at room temperature for 30 minutes. Then methyl 3-chloro-4-[(1-methylethyl)oxy]benzoate (Preparation 2)(2.355 g, 10.30 mmol) was added and the reaction heated at reflux temperature for 1.5 hours. The cooled reaction was evaporated and partitioned between DCM (100 mL) and water (100 mL). The water layer was washed with DCM (50 mL) and the combined DCM layers dried (hydrophobic frit) and evaporated. The crude product was purified by chromatography through a small silica pad, eluting with DCM to yield 1,1-dimethylethyl 5-(5-{3-chloro-4-[(1-methylethyl)oxy]phenyl}-1,2,4-oxadiazol-3-yl)-3,4-dihydro-2(1H)-isoquinoline carboxylate (2.57 g, 5.47 mmol, 80% yield). $^1$H NMR (400 MHz, CDCl$_3$) δ 8.23 (1H, s), 8.05 (1H, d), 7.95 (1H, d), 7.34 (1H, t), 7.27 (1H, d), 7.06 (1H, d), 4.76-4.63 (1H, m), 4.66 (2H, br.s), 3.67 (2H, br.t), 3.25 (2H, br.t), 1.51 (9H, s), 1.45 (6H, d); m/z (API-ES) 414, 416 [M+H-56]$^+$.

PREPARATION 4

1,1-dimethylethyl 5-(5-{3-cyano-4-[(1-methylethyl)oxy]phenyl}-1,2,4-oxadiazol-3-yl)-3,4-dihydro-2(1H)-isoquinolinecarboxylate

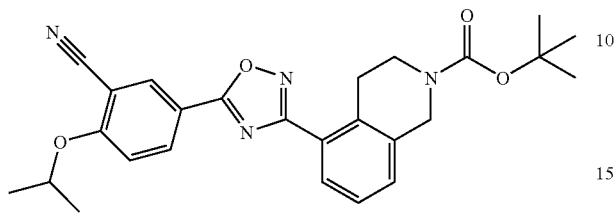

To a solution of 3-cyano-4-[(1-methylethyl)oxy]benzoic acid (can be prepared as described in WO2005/58848, 737 mg, 3.59 mmol) and oxalyl chloride (360 μl) in DCM (20 mL) was added DMF (20 μl). The solution was stirred at room temperature for 90 min, then concentrated in vacuo, and redissolved in dry DMF (6 mL). Separately, 1,1-dimethylethyl 5-[(hydroxyamino)(imino)methyl]-3,4-dihydro-2(1H)-isoquinolinecarboxylate (Preparation 1, 1.05 g, 3.60 mmol), N,N-dimethyl-4-pyridinamine (DMAP) (20 mg) and N,N-diisopropylethylamine (DIPEA) (1.31 ml, 7.50 mmol) were dissolved in DMF (10 mL). 5 mL of the first DMF solution was added to the second solution, and the yellow solution stirred at room temperature for 1 h and then at 95° C. for 18 h. The reaction was concentrated in vacuo then partitioned between DCM (50 mL) and saturated aqueous NaHCO$_3$ (50 mL). The organics were washed with saturated aqueous NaHCO$_3$ (50 mL), then the combined aqueous extracted with DCM (20 mL). The combined organics were concentrated in vacuo to give a crude brown oil. Flash chromatography (gradient [0.5-4%] MeOH in DCM) and concentration in vacuo gave the title compound as a pale yellow solid (512 mg, 37%). $^1$H NMR (400 MHz, CDCl$_3$) δ 8.42 (1H, d), 8.34 (1H, dd), 7.96 (1H, d), 7.34 (1H, t), 7.29 (1H, d), 7.13 (1H, d), 4.80 (1H, sept), 4.67 (2H, s), 3.68 (2H, t), 3.24 (2H, t), 1.51 (9H, s), 1.48 (6H, d); m/z (ES) 361 [M+H-100]$^+$.

PREPARATION 5

Ethyl[5-(5-{3-cyano-4-[(1-methylethyl)oxy]phenyl}-1,2,4-oxadiazol-3-yl)-3,4-dihydro-2(1H)-isoquinolinyl]acetate formic acid salt

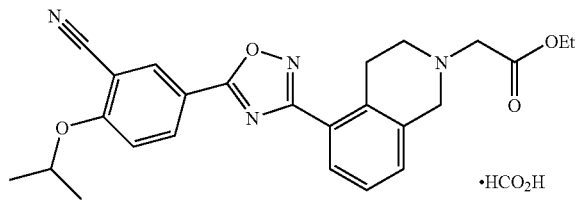

A suspension of 2-[(1-methylethyl)oxy]-5-[3-(1,2,3,4-tetrahydro-5-isoquinolinyl)-1,2,4-oxadiazol-5-yl]benzonitrile (Example 3, 28.8 mg, 0.080 mmol), ethyl bromoacetate (35.5 μl, 0.32 mmol) and Cs$_2$CO$_3$ (130 mg, 0.40 mmol) in DMF (2 mL) was stirred at room temperature for 1 h, and then irradiated to 60° C. for 5 min in the microwave. The suspension was added to an SCX cartridge, and the product eluted with methanolic ammonia. Concentration in vacuo gave a crude product (43 mg) that was purified by MDAP to give the title compound as a clear film (11.6 mg, 32%). $^1$H NMR (400 MHz, CDCl$_3$) δ 8.41 (1H, d), 8.33 (1H, dd), 8.09 (1H, br. s), 8.01 (1H, d), 7.34 (1H, apparent t), 7.21 (1H, d), 7.12 (1H, d), 4.80 (1H, sept), 4.24 (2H, q), 4.00 (2H, s), 3.52 (2H, s), 3.35 (2H, t), 3.07 (2H, t), 1.48 (6H, d), 1.31 (3H, t); m/z (ES) 447 [M+H]$^+$.

PREPARATION 6

Methyl 3-[5-(5-{3-cyano-4-[(1-methylethyl)oxy]phenyl}-1,2,4-oxadiazol-3-yl)-3,4-dihydro-2(1H)-isoquinolinyl]propanoate formic acid salt

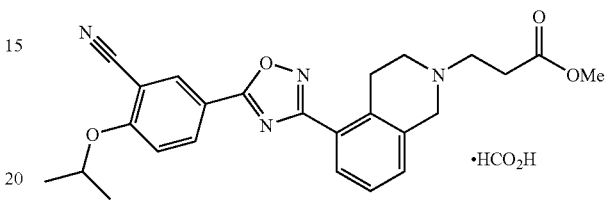

A suspension of 2-[(1-methylethyl)oxy]-5-[3-(1,2,3,4-tetrahydro-5-isoquinolinyl)-1,2,4-oxadiazol-5-yl]benzonitrile (Example 3, 28.8 mg, 0.080 mmol), methyl 3-bromopropionate (35 μl, 0.32 mmol) and Cs$_2$CO$_3$ (130 mg, 0.40 mmol) in DMF (2 mL) was stirred at room temperature for 1 h, and then irradiated to 60° C. for 5 min in the microwave. More methyl 3-bromopropionate (35 μl, 0.32 mmol) was added and the suspension was stirred at room temperature for 3.5 h, and then irradiated to increasing temperatures in the microwave until 150° C. for 30 min was achieved. The suspension was filtered and concentrated in vacuo then purified by MDAP to give the title compound as a yellow film (5.9 mg, 17%). $^1$H NMR (400 MHz, CDCl$_3$) δ 8.42 (1H, d), 8.33 (1H, dd), 8.21 (1H, br. s), 8.04 (1H, d), 7.35 (1H, t), 7.24 (1H, d), 7.13 (1H, d), 4.80 (1H, sept), 3.99 (2H, s), 3.72 (3H, s), 3.38 (2H, t), 3.12-3.06 (4H, m), 2.78 (2H, t), 1.48 (6H, d); m/z (ES) 447 [M+H]$^+$.

PREPARATION 7 ethyl 4-[5-(5-{3-cyano-4-[(1-methylethyl)oxy]phenyl}-1,2,4-oxadiazol-3-yl)-3,4-dihydro-2(1H)-isoquinolinyl]butanoate formic acid salt

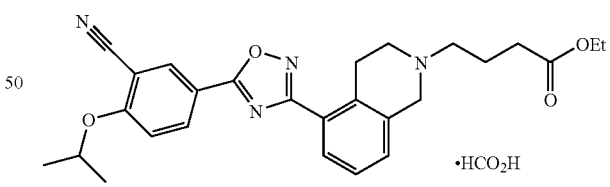

A suspension of 2-[(1-methylethyl)oxy]-5-[3-(1,2,3,4-tetrahydro-5-isoquinolinyl)-1,2,4-oxadiazol-5-yl]benzonitrile (Example 3, 28.8 mg, 0.080 mmol), ethyl 4-bromobutyrate (45.8 μl, 0.32 mmol) and Cs$_2$CO$_3$ (130 mg, 0.40 mmol) in DMF (2 mL) was stirred at room temperature for 1 h, and then irradiated to 60° C. for 5 min in the microwave. More ethyl 4-bromobutyrate (45.8 μl, 0.32 mmol) was added and the suspension was stirred at room temperature for 3.5 h. It was then filtered, concentrated in vacuo and purified by MDAP to give the title compound as a yellow film (8.0 mg, 21%). $^1$H NMR (400 MHz, CDCl$_3$) δ 8.42 (1H, d), 8.34 (1H, dd), 8.27 (br. s), 8.09 (1H, d), 7.39 (1H, t), 7.27 (1H, d), 7.13 (1H, d), 4.80 (1H, sept), 4.19 (2H, s), 4.13 (2H, q), 3.47 (2H, t), 3.28 (2H, t), 2.99 (2H, t), 2.44 (2H, t), 2.10 (2H, quin), 1.48 (6H, d), 1.25 (3H, t); m/z (ES) 475 [M+H]$^+$.

PREPARATION 8

3-Chloro-4-[(1-methylethyl)oxy]benzoyl chloride

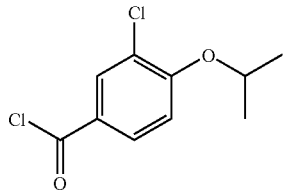

A round bottom flask was charged with 3-chloro-4-[(1-methylethyl)oxy]benzoic acid (available from Paragos Product List, 10.2 g, 47.5 mmol), dichloromethane (158 ml) and oxalyl chloride (8.29 ml, 95 mmol). The reaction mixture was cooled to 0° C. in an ice/water bath prior to the addition of N,N-dimethylformamide (0.158 ml). The solution was allowed to warm to ambient temperature overnight. The solvent was evaporated to yield the title compound as a cream solid (11.4 g).

$^1$H NMR (CHLOROFORM-d) d: 8.14 (d, 1H), 8.00 (dd, 2.5 Hz, 1H), 6.98 (d, 1H), 4.73 (spt, 1H), 1.44 (d, 6H)

PREPARATION 9

2-Methyl-1-(methyloxy)-3-[(E)-2-nitroethenyl]benzene

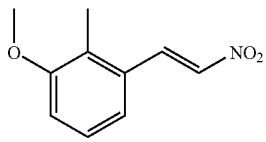

To a solution of 2-methyl-3-(methyloxy)benzaldehyde (available from Allichem Product List; 20 g; 133 mmol) in nitromethane (400 ml) was added ammonium acetate (6.16 g; 80 mmol) and the resulting orange mixture was stirred for 1 h at 100° C. then cooled to room temperature and concentrated in vacuo. The residue was partitioned between ethyl acetate (×2) and brine, and the organic layers washed with brine, dried (MgSO$_4$) and concentrated in vacuo. Trituration with dichloromethane/ether gave the title compound as a yellow solid (6.6 g).

$^1$H NMR (CDCl$_3$) δ: 8.35 (d, 1H), 7.48 (d, 1H), 7.22 (t, 1H), 7.11 (d, 1H), 6.96 (d, 1H), 3.86 (s, 3H), 2.33 (s, 3H)

After evaporation of the mother liquors further product (7.22 g) was obtained by trituration with diethyl ether. The mother liquors were again evaporated, and the residue was purified by chromatography, eluting with 5-10% ethyl acetate in cyclohexane, to give further product (3.45 g) after trituration with ether.

PREPARATION 10

{2-[2-Methyl-3-(methyloxy)phenyl]ethyl}amine

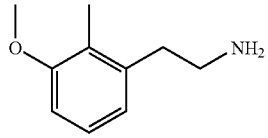

To lithium borohydride (2M in THF; 2.0 ml; 4.0 mmol) (cloudy) at room temperature was added dropwise over 0.5 min chlorotrimethylsilane (1.02 ml; 8.00 mmol). A precipitate was formed and after ca. 3 min, 2-methyl-1-(methyloxy)-3-[(E)-2-nitroethenyl]benzene (Preparation 9, 193 mg; 1.0 mmol) in THF (4 ml) was added dropwise via syringe over 5 min, making sure that the temperature remained at ca. 25° C. (using a water cold bath). The solution was stirred at room temperature overnight. The mixture was cooled with an ice bath, methanol was added slowly, and the solvent removed in vacuo. The residue was partitioned between 25% aqueous sodium hydroxide and dichloromethane. The aqueous phase was separated and extracted three times with dichloromethane and the combined organic layers evaporated. Purification of the residue by solid phase extraction (SCX column), eluting with methanol followed by 2N ammonia in methanol, followed by evaporation of the ammonia containing fraction gave the title compound (80 mg).

$^1$H NMR (CDCl$_3$) δ: 7.10 (t, 1H), 6.78 (d, 1H), 6.73 (d, 1H), 3.81 (s, 3H), 2.91 (t, 2H), 2.77 (t, 2H), 2.18 (s, 3H), 1.76 (br. s., 2H)

PREPARATION 11

{2-[2-Methyl-3-(methyloxy)phenyl]ethyl}formamide

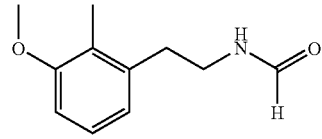

{2-[2-Methyl-3-(methyloxy)phenyl]ethyl}amine (Preparation 10; 1.75 g; 10.6 mmol) was heated under reflux with ethyl formate (97%; 15 ml) for 15 h. Removal of the solvent gave the crude product (ca. 2 g), which was purified by chromatography on silica gel, eluting with a gradient of 13-63% ethyl acetate in cyclohexane, to give the title compound (1.57 g).

MS m/z 194 [MH$^+$]

PREPARATION 12

5-Methyl-6-(methyloxy)-3,4-dihydro-2(1H)-iso-quinolinecarbaldehyde

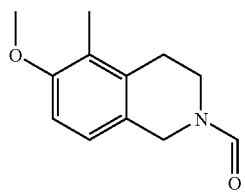

To a solution of {2-[2-methyl-3-(methyloxy)phenyl]ethyl}formamide (Preparation 11; 1.93 g; 10.0 mmol) in formic acid (20 ml) was added paraformaldehyde (0.315 g; 10.5 mmol) and the resulting mixture was heated under reflux (100° C.) for 20 min.

The mixture was cooled quickly to room temperature with ice cold water, and the solvent removed. Purification by chromatography on silica gel, eluting with a gradient of methanol in dichloromethane, gave the title compound as a white solid (1.64 g), which was used without further purification.

MS m/z 206 [MH$^+$]

PREPARATION 13

5-Methyl-1,2,3,4-tetrahydro-6-isoquinolinol

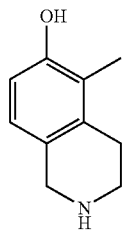

To a solution of 5-methyl-6-(methyloxy)-3,4-dihydro-2(1H)-isoquinolinecarbaldehyde (Preparation 12; 1.49 g; 7.26 mmol) in dichloromethane (25 ml) at 0° C. under nitrogen was slowly added boron tribromide (9.09 g; 36.3 mmol). After 85 min at 0° C., methanol (25 ml) was added slowly, and the resulting mixture was left standing at room temperature for three days. Removal of the solvent and trituration with methanol/dichloromethane gave a white solid residue; the mother liquors were concentrated and the residue applied to an SCX solid phase extraction cartridge (20 g) and eluted with methanol followed by 2N ammonia in methanol to elute the product. After evaporation of the solvent the title compound (780 mg) was obtained as a pale yellow solid.

$^1$H NMR (DMSO-d$_6$) δ: 8.91 (br. s., 1H), 6.62 (d, 1H), 6.56 (d, 1H), 3.70 (s, 2H), 2.92 (t, 2H), 2.48 (t, 2H), 1.96 (s, 3H)

PREPARATION 14

1,1-Dimethylethyl 6-hydroxy-5-methyl-3,4-dihydro-2(1H)-isoquinolinecarboxylate

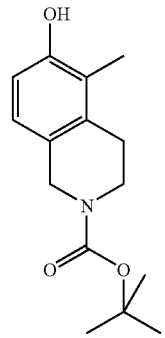

To a suspension of 5-methyl-1,2,3,4-tetrahydro-6-isoquinolinol (Preparation 13; 163 mg; 1.0 mmol) in dichloromethane (5 ml) at 0° C. was added triethylamine (0.21 ml; 1.50 mmol) followed by bis(1,1-dimethylethyl)dicarbonate (240 mg; 1.10 mmol). The solvent was evaporated and the residue partitioned between ethyl acetate and brine. The aqueous layer was further extracted with ethyl acetate and the combined organic layers were dried (MgSO$_4$) and evaporated to give a yellow oil. Purification by flash chromatography eluting with a gradient of 5-25% ethyl acetate in cyclohexane gave the title compound as a white foam (232 mg).

MS m/z 262 [M−H]

PREPARATION 15

1,1-Dimethylethyl 5-methyl-6-{[(trifluoromethyl)sulfonyl]oxy}-3,4-dihydro-2(1H)-isoquinolinecarboxylate

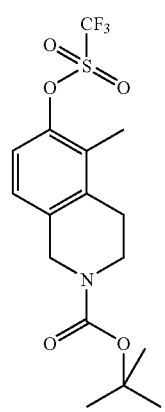

To a solution of 1,1-dimethylethyl 6-hydroxy-5-methyl-3,4-dihydro-2(1H)-isoquinolinecarboxylate (preparation 14; 263 mg; 1.00 mmol) in dichloromethane (5 ml) at −30° C. under nitrogen was added pyridine (0.162 ml; 2.00 mmol) followed by slow addition of trifluoromethanesulphonic anhydride (0.186 ml; 1.10 mmol). After 0.5 h between −30° C. and −20° C., the solvent was removed, and the residue taken up in ethyl acetate. The solution was washed with 1N hydrochloric acid followed by saturated sodium bicarbonate solution, dried (MgSO₄) and concentration in vacuo to give the title compound as a pale yellow oil (368 mg).

MS m/z 394 [M−H]

PREPARATION 16

1,1-Dimethylethyl 6-cyano-5-methyl-3,4-dihydro-2 (1H)-isoquinolinecarboxylate

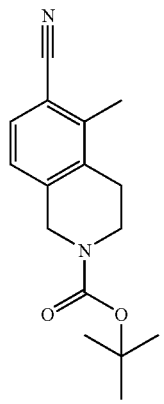

A solution of 1,1-dimethylethyl 5-methyl-6-{[(trifluoromethyl)sulfonyl]oxy}-3,4-dihydro-2(1H)-isoquinolinecarboxylate (Preparation 15; 395 mg; 1.00 mmol) in DMF (4 ml) was de-gassed under high vacuum with stirring for 15 min, followed by addition of zinc cyanide (153 mg; 1.30 mmol) and tetrakis(triphenylphosphine)palladium (0) (116 mg; 0.10 mmol) under nitrogen. The resulting deep yellow mixture was stirred at 100° C. for 6 h. The solvent was removed, the residue dissolved in ethyl acetate, and the solution washed with saturated sodium bicarbonate. The aqueous layer was further extracted with ethyl acetate, and the combined organic layers washed with brine, dried (MgSO₄), and evaporated to give the crude product. Purification by flash chromatography on silica gel, eluting with a gradient of 5-25% ethyl acetate in cyclohexane, gave the title compound (214 mg) as a white solid.

¹H NMR (CDCl₃) δ: 7.44 (d, 1H), 7.04 (d, 1H), 4.60 (s, 2H), 3.69 (t, 2H), 2.75 (t, 2H), 2.46 (s, 3H), 1.49 (s, 9H)

PREPARATION 17

1,1-Dimethylethyl 6-[(hydroxyamino)(imino)methyl]-5-methyl-3,4-dihydro-2(1H)-isoquinolinecarboxylate

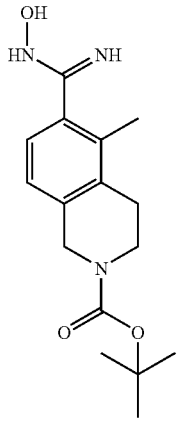

1,1-Dimethylethyl 6-cyano-5-methyl-3,4-dihydro-2(1H)-isoquinolinecarboxylate (Preparation 16; 404 mg; 1.48 mmol) was stirred overnight at 80° C. with hydroxylamine hydrochloride (619 mg; 8.90 mmol) and sodium bicarbonate (748 mg; 8.9 mmol) in ethanol (10 ml). Further sodium bicarbonate (400 mg) and hydroxylamine hydrochloride (300 mg) were added, and heating continued for ca. 8 h. The mixture was cooled to room temperature, and the resulting solid removed, washed with ethanol, and dried under high vacuum to give the title compound as a white solid (431 mg).

¹H NMR (DMSO-d₆) δ: 7.06 (d, 1H), 6.99 (d, 1H), 4.48 (br. s., 2H), 3.58 (t, 2H), 2.67 (t, 2H), 2.19 (s, 3H), 1.42 (s, 9H) (exchangeables not listed; not clearly observed).

PREPARATION 18

1,1-Dimethylethyl 6-[{[({3-chloro-4-[(1-methylethyl)oxy]phenyl}carbonyl)oxy]amino}(imino)methyl]-5-methyl-3,4-dihydro-2(1H)-isoquinolinecarboxylate

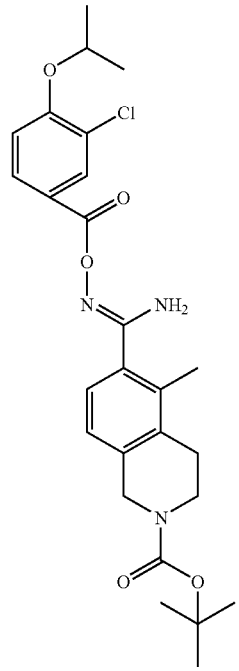

To a solution of 1,1-dimethylethyl 6-[(hydroxyamino)(imino)methyl]-5-methyl-3,4-dihydro-2(1H)-isoquinolinecarboxylate (Preparation 17; 435 mg; 1.42 mmol) in dichloromethane (10 ml) was added triethylamine (0.30 ml; 2.14 mmol) followed by 3-chloro-4-[(1-methylethyl)oxy]benzoyl chloride (Preparation 8; 365 mg; 1.57 mmol) in dichloromethane (5 ml). After 30 min, the reaction was concentrated, and the residue partitioned between ethyl acetate and saturated sodium bicarbonate. The aqueous layer was further extracted with ethyl acetate, and the combined organic layers washed with brine, dried (MgSO₄) and concentrated in vacuo. Purification by flash chromatography on silica gel, eluting with a gradient of 10-50% ethyl acetate in cyclohexane gave the title compound as a white foam (413 mg).

MS m/z 500 [M−H]

PREPARATION 19
1,1-Dimethylethyl 6-(5-{3-chloro-4-[(1-methylethyl)oxy]phenyl}-1,2,4-oxadiazol-3-yl)-5-methyl-3,4-dihydro-2(1H)-isoquinolinecarboxylate

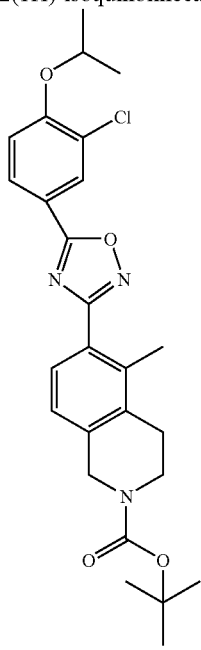

A solution of 1,1-dimethylethyl 6-[{[({3-chloro-4-[(1-methylethyl)oxy]phenyl}carbonyl)oxy]amino}(imino)methyl]-5-methyl-3,4-dihydro-2(1H)-isoquinolinecarboxylate (Preparation 18; 413 mg; 0.823 mmol) in 1,4-dioxane (15 ml) was stirred at 110° C. for ca. 18 h. The mixture was cooled to room temperature and the solvent removed. Purification by flash chromatography on silica gel, eluting with 5-25% ethyl acetate in cyclohexane followed by 13-63% ethyl acetate in cyclohexane, gave the title compound as a white foam (220 mg).
$^1$H NMR (CHLOROFORM-d) δ: 8.24 (d, 1H), 8.05 (dd, 1H), 7.76 (d, 1H), 7.10 (d, 1H), 7.06 (d, 1H), 4.72 (spt, 1H), 4.63 (s, 2H), 3.71 (t, 2H), 2.84 (t, 2H), 2.52 (s, 3H), 1.51 (s, 9H), 1.45 (d, 6H)

PREPARATION 20
Ethyl 3-[6-(5-{3-chloro-4-[(1-methylethyl)oxy]phenyl}-1,2,4-oxadiazol-3-yl)-5-methyl-3,4-dihydro-2(1H)-isoquinolinyl]propanoate

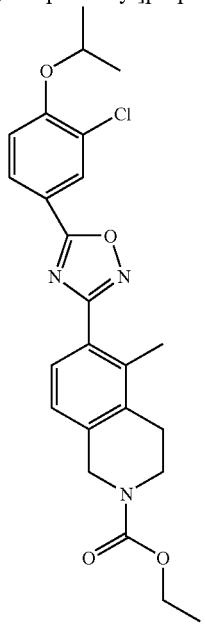

To a suspension of 6-(5-{3-chloro-4-[(1-methylethyl)oxy]phenyl}-1,2,4-oxadiazol-3-yl)-5-methyl-1,2,3,4-tetrahydroisoquinoline trifluoroacetate (Example 10; 90 mg; 0.18 mmol) in acetonitrile (3 ml) was added 1,8-diazabicyclo[5.4.0]undec-7-ene (DBU; 0.16 ml; 1.09 mmol). Ethyl acrylate (0.03 ml; 0.27 mmol) was added to the solution and the resulting mixture stirred at 70° C. for 0.5 h. The mixture was cooled to room temperature and the solvent removed. The residue was partitioned between ethyl acetate and brine, and the aqueous layer further extracted with ethyl acetate. The combined organic layers were washed with brine, dried (MgSO$_4$) and concentrated in vacuo to give the title compound (90 mg).

MS m/z 484 [MH$^+$]

PREPARATION 21
Ethyl[6-(5-{3-chloro-4-[(1-methylethyl)oxy]phenyl}-1,2,4-oxadiazol-3-yl)-5-methyl-3,4-dihydro-2(1H)-isoquinolinyl]acetate

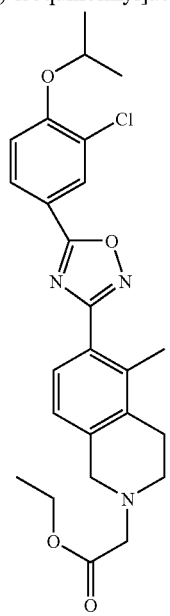

To a suspension of 6-(5-{3-chloro-4-[(1-methylethyl)oxy]phenyl}-1,2,4-oxadiazol-3-yl)-5-methyl-1,2,3,4-tetrahydroisoquinoline trifluoroacetate (Example 10; 90 mg; 0.18 mmol) in DMF (3 ml) under nitrogen at room temperature was added caesium carbonate (177 mg; 0.54 mmol) followed by ethyl bromoacetate (0.026 ml; 0.23 mmol). After 35 min, the mixture was diluted with ethyl acetate and the precipitate removed. The solution was washed with water and the aqueous layer further extracted with ethyl acetate. The organic layer was washed with brine, dried over MgSO$_4$ and concentrated in vacuo to give the title compound (75 mg).

MS m/z 470 [MH$^+$]

PREPARATION 22

1,1-Dimethylethyl 6-(5-{3-cyano-4-[(1-methylethyl)oxy]phenyl}-1,2,4-oxadiazol-3-yl)-5-methyl-3,4-dihydro-2(1H)-isoquinolinecarboxylate

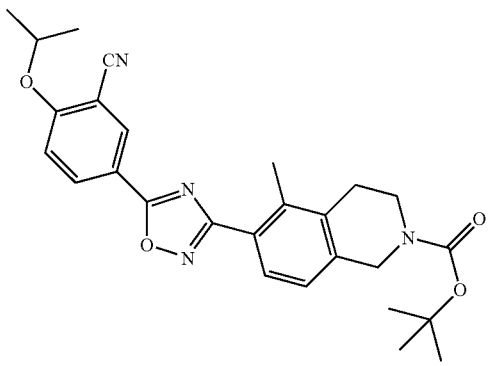

Oxalyl chloride (571 mg, 4.5 mmol) was added to a solution of 3-cyano-4-[(1-methylethyl)oxy]benzoic acid (available from AK Scientific Product Catalog; 800 mg, 3.90 mmol) in dichloromethane (15 ml) followed by DMF (catalytic amount). The reaction mixture was stirred for 45 minutes, further oxalyl chloride (0.1 ml) and DMF (1 drop) were added and stirring continued for 20 minutes. The solvent was evaporated, the residue was co-evaporated with toluene then dried under high vacuum for 30 minutes. The crude acid chloride was dissolved in acetonitrile (10 ml) and added to a suspension of 1,1-dimethylethyl 6-[(hydroxyamino)(imino)methyl]-5-methyl-3,4-dihydro-2(1H)-isoquinolinecarboxylate (Preparation 17; 916 mg, 3.00 mmol) and triethylamine (607 mg, 6.00 mmol) in acetonitrile (15 ml). The reaction mixture was stirred at room temperature for 40 minutes then heated under reflux for 24 hours. The reaction mixture was cooled and the solvent evaporated. The residue was partitioned between ethyl acetate and saturated sodium bicarbonate solution. The organic phase was separated, washed with brine, dried ($MgSO_4$) and evaporated to give the crude product (1.3 g). The residue was purified by chromatography, eluting with 8-38% ethyl acetate in cyclohexane, to give the title compound (486 mg).

$^1$H NMR (CHLOROFORM-d) δ: 8.42 (d, 1H), 8.33 (dd, 1H), 7.76 (d, 1H), 7.12 (d, 1H), 7.11 (d, 1H), 4.80 (spt, 1H), 4.64 (s, 2H), 3.72 (t, 2H), 2.84 (t, 2H), 2.52 (s, 3H), 1.51 (s, 9H), 1.48 (d, 6H)

PREPARATION 23

Ethyl[6-(5-{3-cyano-4-[(1-methylethyl)oxy]phenyl}-1,2,4-oxadiazol-3-yl)-5-methyl-3,4-dihydro-2(1H)-isoquinolinyl]acetate

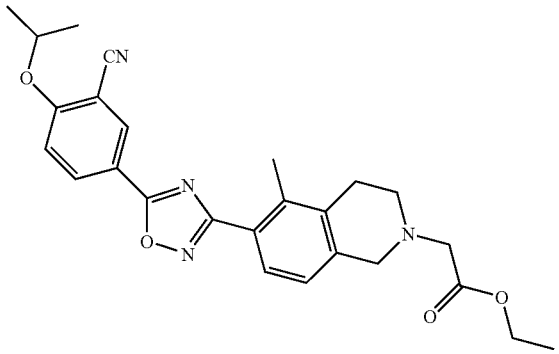

A mixture of 2-[(1-methylethyl)oxy]-5-[3-(5-methyl-1,2,3,4-tetrahydro-6-isoquinolinyl)-1,2,4-oxadiazol-5-yl]benzonitrile trifluoroacetic acid salt (Example 11; 100 mg, 0.20 mmol), ethyl bromoacetate (44 mg, 30 µl, 0.26 mmol) and caesium carbonate (200 mg, 0.61 mmol) in dry DMF (3 ml) was stirred at room temperature for 1 hour. The reaction mixture was diluted with water (10 ml) and extracted with ethyl acetate (3×5 ml). The combined extracts were dried and evaporated. Purification by chromatography on silica gel, eluting with 10% ethyl acetate in cyclohexane gave the title compound as a colourless oil (85 mg). MS m/z 461 [MH]$^+$.

PREPARATION 24

Ethyl 3-[6-(5-{3-cyano-4-[(1-methylethyl)oxy]phenyl}-1,2,4-oxadiazol-3-yl)-5-methyl-3,4-dihydro-2(1H)-isoquinolinyl]propanoate

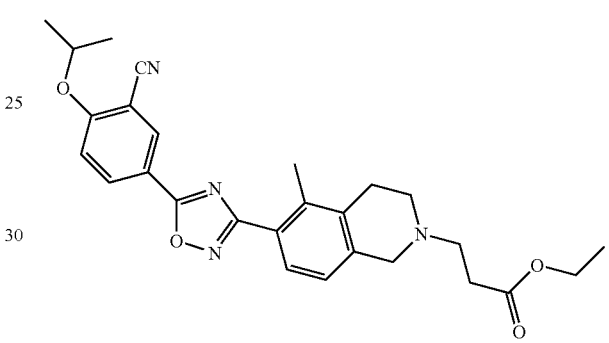

A mixture of 2-[(1-methylethyl)oxy]-5-[3-(5-methyl-1,2,3,4-tetrahydro-6-isoquinolinyl)-1,2,4-oxadiazol-5-yl]benzonitrile trifluoroacetic acid salt (Example 11; 100 mg, 0.20 mmol), ethyl acrylate (31 mg, 33 µl, 0.31 mmol) and 1,8-diazabicyclo[5.4.0]undec-7-ene (DBU; 187 mg, 185 µl, 1.23 mmol) in acetonitrile (3 ml) was stirred at room temperature for 3 hours. The solvent was evaporated and the residue dissolved in ethyl acetate (10 ml); the solution was washed with water (5 ml), dried and evaporated. Purification of the residue by chromatography on silica gel, eluting with 10% ethyl acetate in cyclohexane gave the title compound as a colourless oil (86 mg).

MS m/z 475 [MH]$^+$.

EXAMPLE 1

5-(5-{3-chloro-4-[(1-methylethyl)oxy]phenyl}-1,2,4-oxadiazol-3-yl)-1,2,3,4-tetrahydroisoquinoline hydrochloride

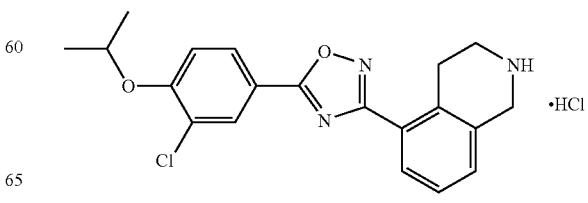

1,1-dimethylethyl 5-(5-{3-chloro-4-[(1-methylethyl)oxy]phenyl}-1,2,4-oxadiazol-3-yl)-3,4-dihydro-2(1H)-isoquinolinecarboxylate (Preparation 3) (2.57 g, 5.47 mmol) was stirred in 4M HCl in 1,4-Dioxane (100 mL). After 1 hour reaction became cloudy and stirring continued for a further 16 hours. Evaporation yielded 5-(5-{3-chloro-4-[(1-methylethyl)oxy]phenyl}-1,2,4-oxadiazol-3-yl)-1,2,3,4-tetrahydroisoquinoline hydrochloride (2.23 g, 5.49 mmol, 100% yield). $^1$H NMR (400 MHz, d$_6$-DMSO) δ 9.43 (2H, s), 8.19 (1H, s), 8.11 (1H dd), 8.03-8.00 (1H, m), 7.51-7.45 (3H, m), 4.89 (1H, sept.), 4.38 (2H, s), 3.43 (2H, t), 3.35-3.32 (2H, m), 1.37 (6H, d); m/z (API-ES) 370, 372 [M+H]$^+$.

EXAMPLE 2

2-[(1-methylethyl)oxy]-5-[3-(1,2,3,4-tetrahydro-5-isoquinolinyl)-1,2,4-oxadiazol-5-yl]benzonitrile hydrochloride

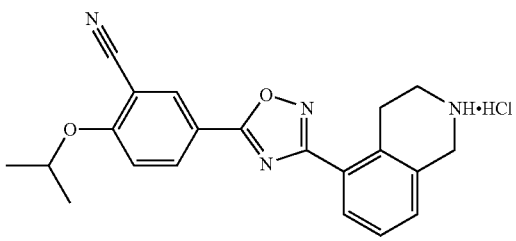

A mixture of 1,1-dimethylethyl 5-(5-{3-cyano-4-[(1-methylethyl)oxy]phenyl}-1,2,4-oxadiazol-3-yl)-3,4-dihydro-2(1H)-isoquinolinecarboxylate (Preparation 4; 53.7 mg, 0.117 mmol) and 4M HCl in dioxane (2 ml) was stirred at room temperature for 64 h. The mixture was concentrated in vacuo, the residue triturated with Et$_2$O and dried in vacuo to leave a light brown solid (35.1 mg, 76%). $^1$H NMR (400 MHz, d$_6$-DMSO) δ 9.52 (2H, br. s), 8.52 (1H, d), 8.40 (1H, dd), 8.02 (1H, dd), 7.57, (1H, d), 7.51-7.48 (2H, m), 4.99 (1H, sept.), 4.38 (2H, s), 3.39-3.34 (4H, m), 1.39 (6H, d); m/z (ES) 361 [M+H]$^+$.

EXAMPLE 3

2-[(1-methylethyl)oxy]-5-[3-(1,2,3,4-tetrahydro-5-isoquinolinyl)-1,2,4-oxadiazol-5-yl]benzonitrile

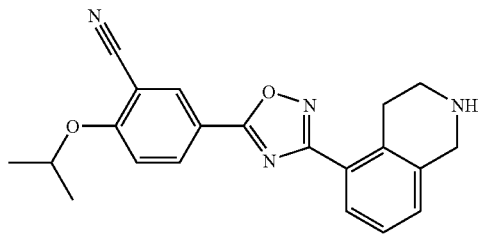

A mixture of 1,1-dimethylethyl 5-(5-{3-cyano-4-[(1-methylethyl)oxy]phenyl}-1,2,4-oxadiazol-3-yl)-3,4-dihydro-2(1H)-isoquinolinecarboxylate (Preparation 4, 512 mg, 1.11 mmol) and 4M HCl in dioxane (20 ml) was stirred at room temperature for 18 h. The mixture was concentrated in vacuo to give a pale yellow solid, which was redissolved in MeOH. This solution was applied to an SCX-3 cartridge (10 g), and the product eluted with 1% NH$_3$ in MeOH. Concentration gave a yellow oil, that became a solid on standing overnight (366 mg, 91%). $^1$H NMR (400 MHz, d$_6$-DMSO) δ 8.38 (1H, d), 8.32 (1H, dd), 7.94 (1H, d), 7.32-7.17 (2H, m), 7.13 (1H, m), 4.80 (1H, sept), 4.10 (2H, s), 3.20-3.14 (4H, m), 1.48 (6H, d); m/z (ES) 361 [M+H]$^+$.

EXAMPLE 4

[5-(5-{3-cyano-4-[(1-methylethyl)oxy]phenyl}-1,2,4-oxadiazol-3-yl)-3,4-dihydro-2(1H)-isoquinolinyl]acetic acid hydrochloride

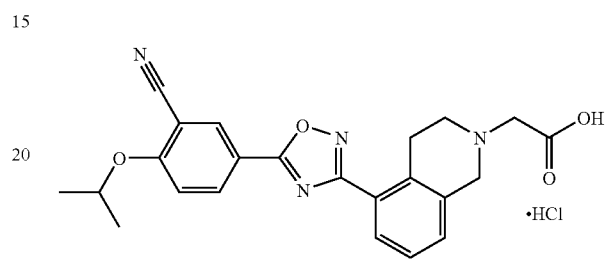

A solution of ethyl[5-(5-{3-cyano-4-[(1-methylethyl)oxy]phenyl}-1,2,4-oxadiazol-3-yl)-3,4-dihydro-2(1H)-isoquinolinyl]acetate formic acid salt (Preparation 5, 11.6 mg, 0.026 mmol) and LiOH (0.3 mg) in THF-MeOH-water (300 μl, 300 μl, 200 μL) was irradiated to 100° C. for 3 min in the microwave. 2M aqueous HCl (1 mL) was added, then the solution extracted with DCM (2×2 mL). The combined organics were concentrated in vacuo to give the title compound as a white solid (10.1 mg, 85%). $^1$H NMR (400 MHz, d$_4$-MeOH) δ 8.48 (1H, d), 8.44 (1H, dd), 8.21 (1H, d), 7.44 (1H, t), 7.47 (2H, apparent d), 4.97 (1H, sept), 4.70 (2H, s), 4.32 (2H, s), 3.67 (2H, t), 3.57 (2H, t), 1.47 (6H, d); m/z (ES) 419 [M+H]$^+$.

EXAMPLE 5

3-[5-(5-{3-cyano-4-[(1-methylethyl)oxy]phenyl}-1,2,4-oxadiazol-3-yl)-3,4-dihydro-2(1H)-isoquinolinyl]propanoic acid hydrochloride

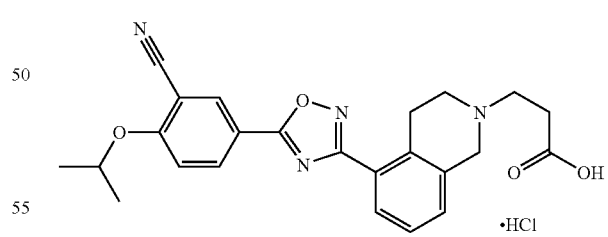

A solution of methyl 3-[5-(5-{3-cyano-4-[(1-methylethyl)oxy]phenyl}-1,2,4-oxadiazol-3-yl)-3,4-dihydro-2(1H)-isoquinolinyl]propanoate formic acid salt (Preparation 6, 5.9 mg, 0.0132 mmol) and LiOH (0.15 mg) in THF-MeOH-water (300 μl, 300 μl, 100 μl) was irradiated to 100° C. for 3 min in the microwave. 2M aqueous HCl (1 ml) and DCM (2 ml) were added sequentially, and a precipitate formed. Filtration gave the title compound as a white solid (6.5 mg, quant.). $^1$H NMR (400 MHz, d$_6$-DMSO) δ 12.71 (1H, br s), 11.41 (1H, br s), 8.53 (1H, d), 8.41 (1H, dd), 8.05 (1H, d), 7.57 (1H, d), 7.53

(1H, t), 7.46 (1H, d), 4.99 (1H, sept), 4.53 (2H, br s), 3.46-3.43 (4H, m), 3.65 (2H, br s), 2.98 (2H, t), 1.39 (6H, d); m/z (ES) 433 [M+H$^+$].

EXAMPLE 6

4-[5-(5-{3-cyano-4-[(1-methylethyl)oxy]phenyl}-1,2,4-oxadiazol-3-yl)-3,4-dihydro-2(1H)-isoquinolinyl]butanoic acid hydrochloride

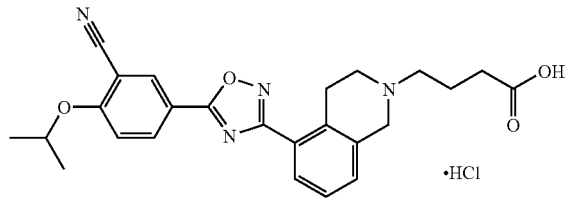

The title compound was made in similar fashion to Example 4, replacing ethyl[5-(5-{3-cyano-4-[(1-methylethyl)oxy]phenyl}-1,2,4-oxadiazol-3-yl)-3,4-dihydro-2(1H)-isoquinolinyl]acetate with ethyl 4-[5-(5-{3-cyano-4-[(1-methylethyl)oxy]phenyl}-1,2,4-oxadiazol-3-yl)-3,4-dihydro-2(1H)-isoquinolinyl]butanoate formic acid salt (Preparation 7, 8.0 mg). The title compound was obtained as a white solid (10.1 mg).

$^1$H NMR (400 MHz, d$_4$-MeOH) δ 8.36 (1H, d), 8.33 (1H, dd), 8.23 (1H, d), 7.43 (1H, t), 7.37 (1H, d), 7.35 (1H, d), 4.85 (1H, sept), 4.52 (2H, br s), 3.63-3.54 (4H, br. m), 3.30 (2H, apparent dd), 2.43 (2H, t), 2.06 (2H, quin), 1.36 (6H, d); m/z (ES) 447 [M+H]$^+$.

EXAMPLE 7

2-[(1-methylethyl)oxy]-5-[3-(2-methyl-1,2,3,4-tetrahydro-5-isoquinolinyl)-1,2,4-oxadiazol-5-yl]benzonitrile

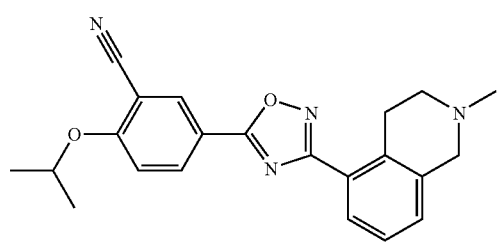

To a solution of 2-[(1-methylethyl)oxy]-5-[3-(1,2,3,4-tetrahydro-5-isoquinolinyl)-1,2,4-oxadiazol-5-yl]benzonitrile (Example 3, 25.0 mg, 0.069 mmol) and formaldehyde (37% w/v in H$_2$O, 8.0 μL, 0.10 mmol) in DCM (5 mL) was added NaBH(OAc)$_3$ (29 mg, 0.14 mmol) and the resulting solution stirred at room temperature for 20 min. Brine (5 mL) was added, and the aqueous extracted with DCM (5 mL). The combined organics were concentrated in vacuo to give a white solid. This solid was redissolved in DMSO-MeOH, added to an SCX cartridge and washed with MeOH. The product was eluted with NH$_3$ in MeOH; concentration in vacuo gave a white solid (20.1 mg, 78%). $^1$H NMR (400 MHz, CDCl$_3$) δ 8.41 (1H, d), 8.32 (1H, dd), 7.98 (1H, d), 7.29 (1H, t), 7.20 (1H, d), 7.12 (1H, d), 4.79 (1H, sept), 3.67 (2H, s), 3.30 (2H, t), 2.75 (2H, t), 2.49 (3H, s), 1.47 (6H, d).

EXAMPLE 8

3-[6-(5-{3-Chloro-4-[(1-methylethyl)oxy]phenyl}-1,2,4-oxadiazol-3-yl)-5-methyl-3,4-dihydro-2(1H)-isoquinolinyl]propanoic acid

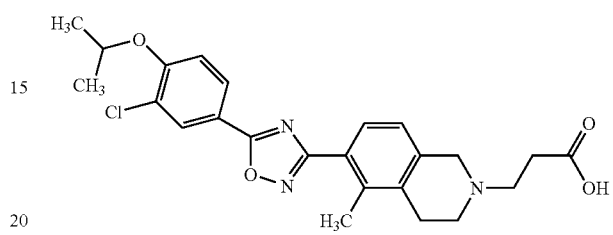

To a solution of ethyl 3-[6-(5-{3-chloro-4-[(1-methylethyl)oxy]phenyl}-1,2,4-oxadiazol-3-yl)-5-methyl-3,4-dihydro-2(1H)-isoquinolinyl]propanoate (Preparation 20; 90 mg; 0.186 mmol) in ethanol (2 ml) and THF (2 ml) at room temperature was added 2N sodium hydroxide (0.186 ml; 0.372 mmol), and the resulting mixture was stirred at room temperature for ca. 2.5 h. Removal of most of the solvents, dilution with ca. 1 ml of water, followed by addition of acetic acid (ca. 300 μl) gave a precipitate. The mixture was extracted with dichloromethane to give, after removal of the solvent and trituration with diethyl ether, the title compound as a white solid (40 mg).

$^1$H NMR (DMSO-d$_6$) δ: 8.15 (d, 1H), 8.09 (dd, 1H), 7.64 (d, 1H), 7.43 (d, 1H), 7.09 (d, 1H), 4.88 (spt, 1H), 3.64 (s, 2H), 2.76 (br. s., 4H), 2.72 (t, 2H), 2.44 (t, 2H), 2.41 (s, 3H), 1.36 (d, 6H)

MS m/z 456 [MH$^+$]

EXAMPLE 9

[6-(5-{3-Chloro-4-[(1-methylethyl)oxy]phenyl}-1,2,4-oxadiazol-3-yl)-5-methyl-3,4-dihydro-2(1H)-isoquinolinyl]acetic acid

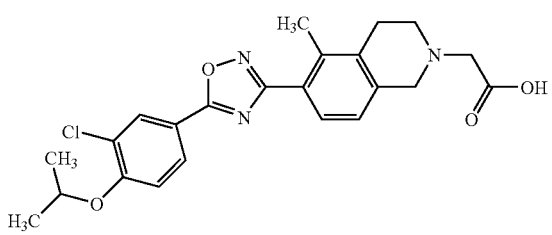

To a solution of ethyl[6-(5-{3-chloro-4-[(1-methylethyl)oxy]phenyl}-1,2,4-oxadiazol-3-yl)-5-methyl-3,4-dihydro-2(1H)-isoquinolinyl]acetate (Preparation 21; 75 mg; 0.16 mmol) in ethanol (2 ml) and THF (2 ml) at room temperature was added 2N sodium hydroxide, and the resulting mixture was stirred at room temperature for 40 min. The solvents were removed and the residue dissolved in water (ca. 1 ml). Acetic acid (1 ml) was added, all solvents were removed and the residue co-evaporated with toluene to give a pale yellow solid. This solid was triturated with diethyl ether to give the title compound, which was filtered off as a pale yellow solid (50 mg).

MS m/z 442 [MH+]

$^1$H NMR (DMSO-d$_6$) δ: 8.16 (br. s., 1H), 8.10 (d, 1H), 7.62 (d, 1H), 7.44 (d, 1H), 7.05 (d, 1H), 4.88 (spt, 1H), 3.70 (br. s., 2H), 2.91 (br. s., 2H), 2.77 (br. s., 4H), 2.42 (br. s., 3H), 1.36 (d, 6H).

EXAMPLE 10

6-(5-{3-Chloro-4-[(1-methylethyl)oxy]phenyl}-1,2,4-oxadiazol-3-yl)-5-methyl-1,2,3,4-tetrahydroisoquinoline trifluoroacetate

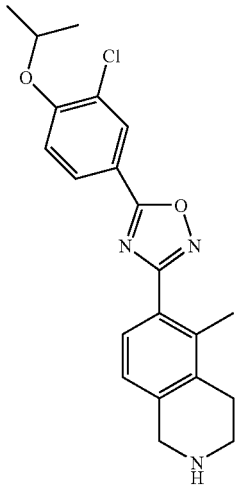

To a solution of 1,1-dimethylethyl 6-(5-{3-chloro-4-[(1-methylethyl)oxy]phenyl}-1,2,4-oxadiazol-3-yl)-5-methyl-3,4-dihydro-2(1H)-isoquinolinecarboxylate (Preparation 19; 210 mg; 0.434 mmol) in dichloromethane (3 ml) at 0° C. was added trifluoroacetic acid (3 ml) dropwise. The resulting mixture was stirred at 0° C. for 1 h, giving a pale yellow solution. Removal of the solvent and co-evaporation with toluene gave a white solid, which was triturated with diethyl ether to give the title compound as a white solid (206 mg).

$^1$H NMR (DMSO-d$_6$) δ: 9.08 (br. s., 2H), 8.17 (d, 1H), 8.10 (dd, 1H), 7.78 (d, 1H), 7.45 (d, 1H), 7.28 (d, 1H), 4.84-4.94 (m, 1H), 4.38 (br. s., 2H), 3.45-3.52 (m, 2H), 2.98 (t, 2H), 2.46 (s, 3H), 1.36 (d, 6H)

MS m/z 384 [MH+]

EXAMPLE 11

2-[(1-Methylethyl)oxy]-5-[3-(5-methyl-1,2,3,4-tetrahydro-6-isoquinolinyl)-1,2,4-oxadiazol-5-yl]benzonitrile trifluoroacetic acid salt

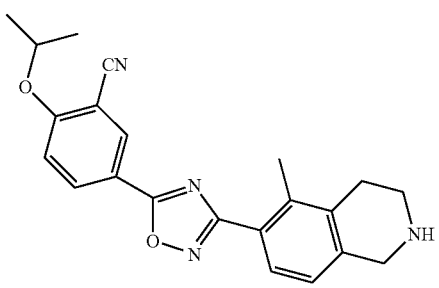

Trifluoroacetic acid (3 ml) was added to an ice cooled solution of 1,1-dimethylethyl 6-(5-{3-cyano-4-[(1-methylethyl)oxy]phenyl}-1,2,4-oxadiazol-3-yl)-5-methyl-3,4-dihydro-2(1H)-isoquinolinecarboxylate (Preparation 22; 486 mg, 1.02 mmol) in dichloromethane (3 ml). The reaction mixture was stirred at 0° C. for 30 minutes. The solvent was evaporated and the residue co-evaporated from toluene (×2). Trituration of the residue with diethyl ether gave the title compound as a colourless solid which was filtered off and dried (485 mg). $^1$H NMR (400 MHz, CDCl$_3$) δ: 1.48 (6H, d), 2.54 (3H, s), 3.09 (2H, m), 3.5 (2H, obscured by residual solvent), 4.36 (2H, s), 4.80 (1H, m), 7.08-7.15 (2H, m), 7.85 (1H, d), 8.33 (1H, d), 8.42 (1H, s), 10.20 (2H, br s). MS m/z 375 [MH]+.

EXAMPLE 12

[6-(5-{3-Cyano-4-[(1-methylethyl)oxy]phenyl}-1,2,4-oxadiazol-3-yl)-5-methyl-3,4-dihydro-2(1H)-isoquinolinyl]acetic acid

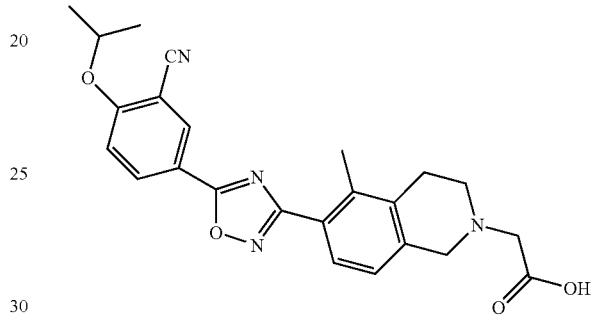

2M Sodium hydroxide (2 ml) was added to a suspension of ethyl[6-(5-{3-cyano-4-[(1-methylethyl)oxy]phenyl}-1,2,4-oxadiazol-3-yl)-5-methyl-3,4-dihydro-2(1H)-isoquinolinyl] acetate (Preparation 23; 80 mg, 0.17 mmol) in ethanol (2 ml). The reaction mixture was stirred at room temperature for 2 hours. The solvent was evaporated and the residue diluted with water (5 ml). The solution was acidified with acetic acid and extracted with ethyl acetate (3×5 ml). The aqueous phase was evaporated and the residue purified by MDAP to give the title compound as a colourless solid (7 mg). $^1$H NMR (400 MHz, d$_4$MeOH) δ: 1.46 (6H, d), 2.55 (3H, s), 3.19 (2H, t), 3.35 (2H, s), 3.67 (2H, t), 3.78 (2H, s), 4.53 (2H, s), 4.95 (1H, m) (part obscured by water peak), 7.20 (1H, d), 7.54 (1H, d), 7.85 (1H, d), 8.50-8.60 (2H, m).

MS m/z 433 [MH]+.

EXAMPLE 13

3-[6-(5-{3-Cyano-4-[(1-methylethyl)oxy]phenyl}-1,2,4-oxadiazol-3-yl)-5-methyl-3,4-dihydro-2(1H)-isoquinolinyl]propanoic acid sodium salt

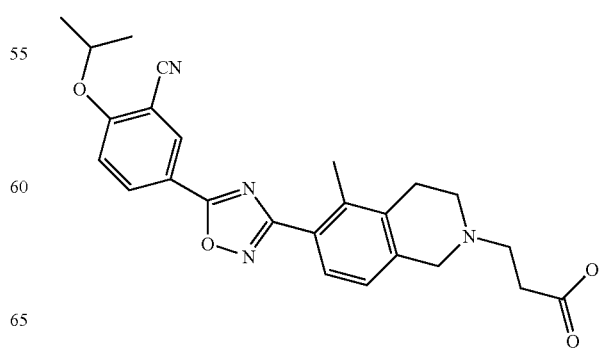

2M sodium hydroxide (2 ml) was added to a solution of ethyl 3-[6-(5-{3-cyano-4-[(1-methylethyl)oxy]phenyl}-1,2,4-oxadiazol-3-yl)-5-methyl-3,4-dihydro-2(1H)-isoquinolinyl]propanoate (Preparation 24; 80 mg, 0.17 mmol) in ethanol (2 ml) at 60° C. The reaction mixture was stirred at 60° C. for 2 hours, cooled to room temperature and diluted with water (2 ml). The solid was filtered off, washed with a small amount of water and dried to give the title compound as a colourless solid (55 mg). $^1$H NMR (400 MHz, d$_6$DMSO) δ: 1.39 (6H, d), 2.08 (2H, t), 2.44 (3H, s), 2.59-2.78 (6H, m), 3.56 (2H, s), 4.98 (1H, m), 7.09 (1H, d), 7.55 (1H, d), 7.65 (1H, d), 8.40 (1H, dd), 8.50 (1H, s). MS m/z 447 [MH]$^+$.

Membrane Preparation for S1P1 GTPγS Assay

For membrane preparations all steps were performed at 4° C. Rat hepatoma cells stably expressing the human S1P1 receptor or Rat Basophilic Leukaemia cells (RBL) stably expressing human S1P3 receptor were grown to 80% confluency before being harvested into 10 ml Phospho-Buffered Saline (PBS) and centrifuged at 1200 rpm for 5 minutes. After removal of the supernatant, the pellet was re-suspended and cells were homogenised within a glass Waring blender for 2 bursts of 15 secs in 200 mls of buffer (50 mM HEPES, 1 mM leupeptin, 25 μg/ml bacitracin, 1 mM EDTA, 1 mM PMSF, 2 μM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

Alternative Membrane Preparation for S1P1 GTPγS Assay

All steps were performed at 4° C. Cells were homogenised within a glass Waring blender for 2 bursts of 15 secs in 200 mls of buffer (50 mM HEPES, 1 mM leupeptin, 25 μg/ml bacitracin, 1 mM EDTA, 1 mM PMSF, 2 μM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

S1P1 GTPγS Assay

Human S1P1 rat hepatoma membranes (1.5 μg/well) were adhered to a wheatgerm agglutinin (WGA)-coated scintillation proximity assay (SPA) beads (0.125 mg/well) in assay buffer (HEPES 20 mM, MgCl$_2$ 10 mM, NaCl 100 mM and pH adjusted to 7.4 using KOH 5M, GDP 10 μM FAC (final assay concentration) and saponin 90 μg/ml FAC was also added).

After 30 minutes pre-coupling on ice the bead and membrane suspension was dispensed into a white Greiner polypropylene LV384-well plate (5 μl/well), containing 0.1 μl of the compound. 5 μl/well [$^{35}$S]-GTPγS (0.5 nM final radioligand conc) made up in assay buffer was then added to agonist plates. The final assay cocktail (10.1 μl) was then centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Alternative Method for S1P1 GTPγS Assay

S$_1$P$_1$ expressing RH7777 membranes (1.5 μg/well) membranes (1.5 μg/well) were homogenised by passing through a 23G needle. These were then adhered to WGA-coated SPA beads (0.125 mg/well) in assay buffer (HEPES 20 mM, MgCl$_2$ 10 mM, NaCl 100 mM and pH adjusted to 7.4 using KOH 5M). GDP 10 μM FAC and saponin 90 μg/ml FAC were also added.

After 30 minutes precoupling on ice, the bead and membrane suspension was dispensed into white Greiner polypropylene LV 384-well plates (5 μl/well), containing 0.1 μl of compound. 5 μl/well [$^{35}$S]-GTPγS (0.5 nM for S$_1$P$_1$ or 0.3 nM for S$_1$P$_3$ final radioligand concentration) made in assay buffer was then added to the plates. The final assay cocktail (10.1 μl) was then sealed, spun on a centrifuge, then read immediately on a Viewlux instrument.

Exemplified compounds of the invention had a pEC50>5. Examples 1-7, 8, 9, 11-13 had a pEC50 of >7. Examples 2, 4, 6 and 8 had a pEC50 of >8,

S1P3

S1P3 membranes from rat basophilic leukaemia cells (RBL-2H3)(1.5 μg/well) were adhered to WGA-coated SPA beads (0.125 mg/well) in assay buffer (HEPES 20 mM, MgCl$_2$ 3 mM, NaCl 100 mM and pH adjusted to 7.4 using KOH 5M), GDP 10 μM FAC and saponin 90 μg/ml FAC was also added).

After 30 minutes pre-coupling on ice the bead and membrane suspension was dispensed into a white Greiner polypropylene LV384-well plate (5 μl/well), containing 0.1 μl of the compound. 5 μl/well [$^{35}$S]-GTPγS (0.5 nM final radioligand conc) made up in assay buffer was then added to agonist plates. The final assay cocktail (10.1 μl) was centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Alternative Method for S1P3 GTPγS Assay

S$_1$P$_3$ expressing RBL membranes (1.5 μg/well) were homogenised by passing through a 23G needle. These were then adhered to WGA-coated SPA beads (0.125 mg/well) in assay buffer (HEPES 20 mM, MgCl$_2$ 10 mM, NaCl 100 mM and pH adjusted to 7.4 using KOH 5M). GDP 10 μM FAC and saponin 90 μg/ml FAC were also added After 30 minutes precoupling on ice, the bead and membrane suspension was dispensed into white Greiner polypropylene LV 384-well plates (5 μl/well), containing 0.1 μl of compound. 5 μl/well [$^{35}$S]-GTPγS (0.5 nM for S$_1$P$_1$ or 0.3 nM for S$_1$P$_3$ final radioligand concentration) made in assay buffer was then added to the plates. The final assay cocktail (10.1 μl) was then sealed, spun on a centrifuge, then read immediately on a Viewlux instrument.

Exemplified compounds tested in this assay had a pEC50<6, many had a pEC50<5. Examples 1, 4, 8-10, 12 and 13 had a pEC50<5.

The invention claimed is:

1. A compound of formula (I) or a pharmaceutically acceptable salt thereof:

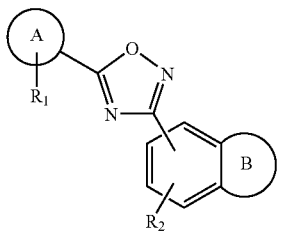

(I)

wherein
A is phenyl;
$R_1$ is up to two substituents independently selected from chloro, isopropoxy, and cyano;
$R_2$ is hydrogen or methyl;
B is:

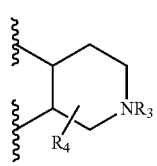

(a)

$R_3$ is hydrogen, methyl or $(CH_2)_{1-3}CO_2H$;
$R_4$ is hydrogen.

2. A compound selected from:
5-(5-{3-chloro-4-[(1-methylethyl)oxy]phenyl}-1,2,4-oxadiazol-3-yl)-1,2,3,4-tetrahydroisoquinoline;
2-[(1-methylethyl)oxy]-5-[3-(1,2,3,4-tetrahydro-5-isoquinolinyl)-1,2,4-oxadiazol-5-yl ]benzonitrile;
[5-(5-{3-cyano-4-[(1-methylethyl)oxy]phenyl}-1,2,4-oxadiazol-3-yl)-3,4-dihydro-2(1H)-isoquinolinyl]acetic acid;
3-[5-(5-{3-cyano-4-[(1-methylethy)oxy]phenyl}-1,2,4-oxadiazol-3-yl)-3,4-dihydro-2(1H)-isoquinolinyl]propanoic acid;
4[-(5-{3-cyano-4-[(1-methylethyl)oxy]phenyl}-1,2,4-oxadiazol-3-yl)-3,4-dihydro-2(1H)-isoquinolinyl]butanoic acid;
2-[(1-methylethl)oxy]-5-[3-(2-methyl-1,2,3,4-tetrahydro-5-isoquinolinyl)-1,2,4-oxadiazol-5-yl]benzonitrile;
[8-(5-{3-Chloro-4-[(1-methylethyl)oxy]phenyl}-1,2,4-oxadiazol-3-yl)-3,4-dihydro-2H-chromen-4-yl]acetic acid;
3-[6-(5-{3-Chloro-4-[(1-methylethyl)oxy]phenyl}-1,2,4-oxadiazol-3-yl)-5-methyl-3,4dihydro-2(1H)-isoquinolinyl]propanoic acid;
[6-(5-{3-Chloro-4-[(1-methylethyl)oxy]phenyl}-1,2,4-oxadiazol-3-yl)-5-methyl-3,4-dihydro-2(1H)-isoquinolinyl]acetic acid;
6-(5-{3-Chloro-4-[(1-methylethyl)oxy]phenyl}-1,2,4-oxadiazol-3-yl)-5-methyl-1,2,3,4tetrahydroisoquinoline;
2-[(1-Methylethyl)oxy]-5-[3-(5-methyl-1,2,3,4-tetrahydro-6-isoquinolinyl)-1,2,4-oxadiazol-5-yl]benzonitrile;
[6-(5-{3-Cyano-4-[(1-methylethyl)oxy]phenyl}-1,2,4-oxadiazol-3-yl)-5-methyl-3,4-dihydro-2(1H)-isoquinolinyl]acetic acid;
3[6-(5-{3-cyano-4-[(1-methylethyl)oxy]phenyl}-1,2,4-oxadiazol-3-yl)-5-methyl-3,4dihydro-2(1H)-isoquinolinyl]propanoic acid;
or a pharmaceutically acceptable salts thereof.

3. A pharmaceutical composition comprising a compound according to claim 1.

* * * * *